United States Patent
Carroll et al.

[11] Patent Number: 6,086,574
[45] Date of Patent: Jul. 11, 2000

[54] FLUID DELIVERY SYSTEMS WITH DIPTUBE CONNECTOR

[75] Inventors: David C. Carroll, Nibley; Pat Draper, Logan, both of Utah

[73] Assignee: Hyclone Laboratories, Inc., Logan, Utah

[21] Appl. No.: 08/975,767

[22] Filed: Nov. 21, 1997

[51] Int. Cl.[7] .................................................. A61M 39/10
[52] U.S. Cl. ........................ 604/533; 604/403; 604/905
[58] Field of Search ................................... 604/203, 403, 604/905, 326, 533, 410

[56] References Cited

U.S. PATENT DOCUMENTS

| | | |
|---|---|---|
| 4,340,052 | 7/1982 | Dennehey et al. . |
| 4,362,204 | 12/1982 | Moore et al. . |
| 4,828,554 | 5/1989 | Griffin ..................................... 604/350 |
| 4,867,739 | 9/1989 | Kawano . |
| 5,137,527 | 8/1992 | Miller et al. . |
| 5,259,843 | 11/1993 | Watanabe et al. . |
| 5,342,345 | 8/1994 | Spencer . |
| 5,364,384 | 11/1994 | Grabenkort et al. . |
| 5,391,163 | 2/1995 | Christine et al. . |
| 5,458,593 | 10/1995 | Macabasco et al. . |
| 5,498,253 | 3/1996 | Aswad et al. . |
| 5,569,222 | 10/1996 | Haselhorst et al. . |

*Primary Examiner*—Glenn K. Dawson
*Assistant Examiner*—Kelly M Cheney
*Attorney, Agent, or Firm*—Workman, Nydegger and Seeley

[57] ABSTRACT

A fluid delivery system includes a flexible media bag having an outlet spout projecting therefrom. A passageway longitudinally extends through the outlet spout and communicates with the interior of the media bag. A diptube connector is mounted to the outlet spout. The diptube connector includes a stem having a first end with a barb radially projecting out therefrom and an opposing second end with an annular flange radially projecting out therefrom. The flange has an outer diameter greater than the inner diameter of the passageway in the outlet spout. The first end of the diptube connector is received in sealed engagement within the first end of the diptube. The second end of the diptube is passed through the passageway in the outlet spout such that the flange on the diptube connector rests on the outlet spout. The outlet spout having the diptube connector mounted thereon is received in sealed engagement within a delivery tube.

26 Claims, 5 Drawing Sheets

FLUID DELIVERY SYSTEMS WITH DIPTUBE CONNECTOR

BACKGROUND OF THE INVENTION

1. The Field of the Invention

The present invention relates to fluid delivery systems and, more specifically, diptube connectors for use in sterile fluid delivery systems.

2. Present State of the Art

Breakthroughs in the biological, pharmaceutical, and chemical fields are occurring at a rapid rate. As a result of the substantial research taking place and the many new applications introduced thereby, large amounts of sterile fluid materials are consumed. Cell culture media used in the biological field is one example of a sterile, fluid material. Scientists and technicians often require cell culture media for use in propagating cell and tissue cultures. Cell culture media is typically a solution of amino acids, electrolytes, serum, serum fractions, vitamins, and growth factors.

Practical use of sterile fluid materials requires that the fluids be dispensable in both an accurate and rapid fashion. Furthermore, the fluids must be dispensable in a fashion to maintain sterility. Even a slight breach of the sterile system can result in extensive costs resulting from contamination of large quantities of sterile material and the destruction of experiments or developments of cell cultures.

Dispensing of sterile fluids has been performed in a variety of different fashions. In one embodiment, a collapsible bag is used having an outlet tube attached thereto. The bag is supported while an exterior pump is used to draw the sterile fluid out through the outlet tube.

Figure 1:
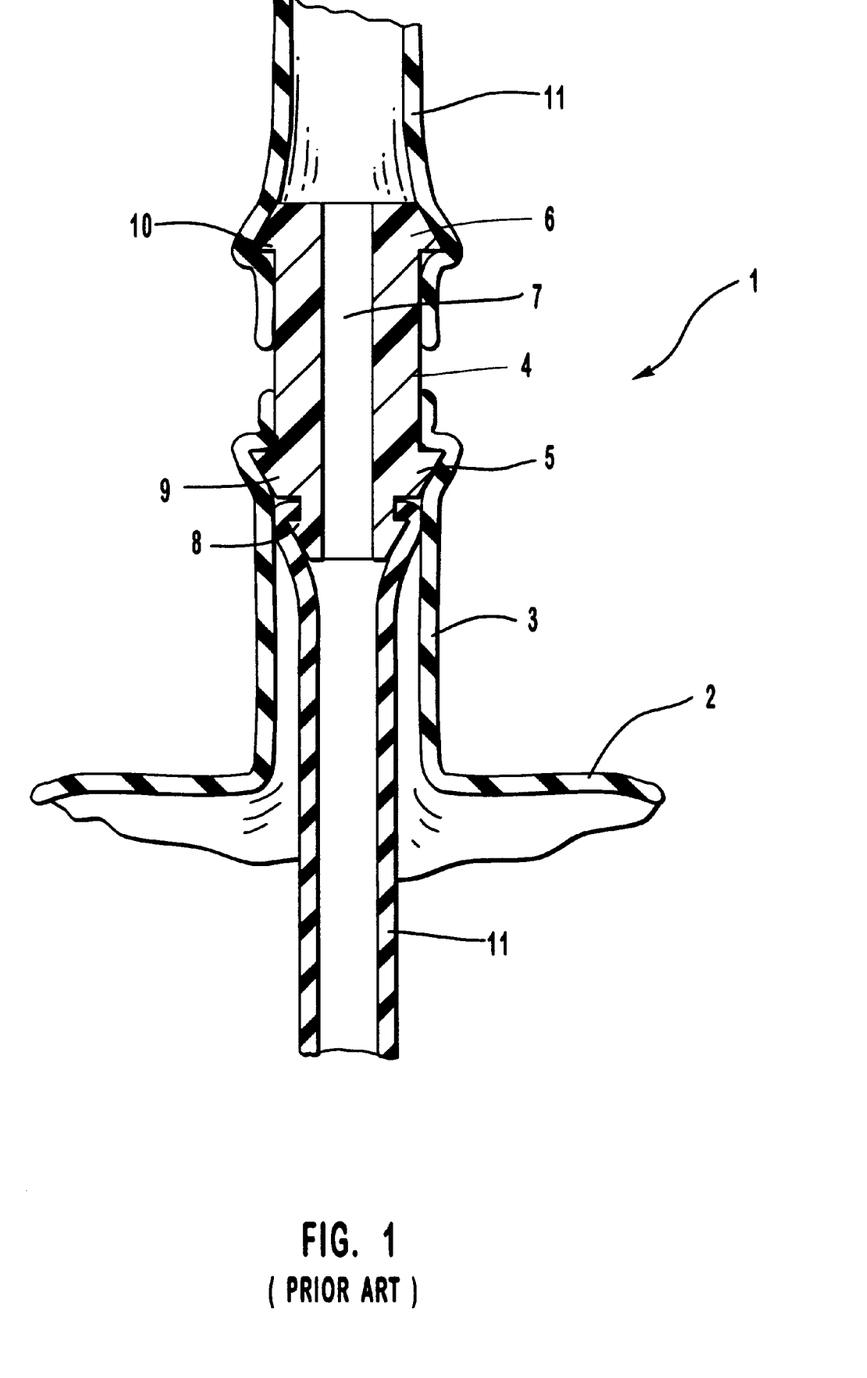
FIG. 1 is a cross-sectional side view of a prior art fluid delivery system using a multi-barb adapter.

A diptube is used to withdraw the fluid from the bottom of the bag, thereby enabling removal of substantially all of the sterile fluid. The diptube comprises a tube having a first end fluid coupled with the outlet tube and a second end positioned at the bottom of the bag. Fluid exiting the bag enters the diptube at the bottom of the bag and then travels to the outlet tube from which it is eventually dispensed. The diptube is traditionally attached to the outlet tube using a multi-barb adapter. For example, depicted in FIG. 1 is one embodiment of a prior art fluid delivery system 1. Fluid delivery system 1 comprises a bag 2 having an outlet tube 3 projecting therefrom. Attached to the end of outlet tube 3 is a multi-barb adapter 4. Adapter 4 has a first end 5, an opposing second end 6, and a passageway 7 extending therebetween. Formed at first end 5 of adapter 4 is a small hose barb 8. Spaced back from small hose barb 8 is a large hose barb 9. A similar large hose barb 10 is positioned at second end 6.

During assembly, small hose barb 8 is received within the first end of a diptube 11 while large hose barb 9 is received within the end of outlet tube 3. The opposing large hose barb 10 is received within the end of a delivery tube 11. In this configuration, fluid travels from diptube 11 through the passageway in adapter 4, and out through delivery tube 11.

Although functional, use of conventional multi-barb adapters, such as adapter 4, has produced contamination problems for the sterile system. Such adapters are typically manufactured from plastic using an injection molding process. Because of the required multiple barbs, and particularly the multiple barbs at one end thereof, the molds for the adapter must necessarily open along the longitudinally axis of the adapter. The molds are prevented from separating along a plane transverse to the longitudinal axis since the barbs would catch within the molds. As a result of the molds opening along the longitudinal axis, seam lines or ridges are formed longitudinally across each of the barbs. These seam lines create minute passageways between the surface of the barb and the corresponding tube received over the barb. Such passageways enable microscopic contaminates to pass from the exterior to the interior of the sterile system, thereby contaminating the system.

Another problem with multi-barb adapters is that they are designed to connect with select sizes of hoses and diptubes. During manufacture, however, it is desirable to produce fluid delivery systems having different tube sizes to accommodate different flow rates. To accommodate different tube sizes, different adapters of different barb sizes must be used. Accordingly, a variety of different sized adapters must be manufactured and inventoried. Furthermore, in some designs it is desirable not to have a diptube.

OBJECTS AND BRIEF SUMMARY OF THE INVENTION

Accordingly, it is an object of the present invention to provide improved diptube connectors for fluid delivery systems.

Another object of the present invention is to provide improved diptube connectors that do not have mold seam lines longitudinally extending across the barbs thereof.

Still another object of the present invention is to provide improved diptube connectors that do not use a multiple barb configuration.

Yet another object of the present invention is to provide diptube connectors that can be easily exchanged to fit a variety of different sized diptubes.

Finally, another object of the present invention is to provide diptube connectors that can be removed when a diptube is not required.

To achieve the foregoing objects, and in accordance with the invention as embodied and broadly described herein, an improved fluid deliver system is provided. The fluid delivery system includes a collapsible media bag having a port connector attached thereto. The port connector comprises a spout having a first end with an annular barb radially outwardly projecting therefrom and an opposing second end with a port plate radially outwardly projecting therefrom. A passageway longitudinally extends through the port connector and communicates with the interior compartment of the media bag.

Removably mounted to the port connector is a diptube connector. The diptube connector comprises a stem having a first end with a barb radially outwardly projecting therefrom and an opposing second end with a mounting flange radially outwardly projecting therefrom. A channel longitudinally extends between the first and second ends of the diptube connector. The first end of the stem is configured to be received in sealed engagement within the first end of a diptube. In this position, the second end of the diptube can be slid into the media bag through the passageway in the port connector. The flange at the second end of the diptube connector has an outside diameter greater than the inside diameter of the passageway in the port connector. Accordingly, the flange biases against the first end of the port connector so as to suspend the diptube within the media bag.

The first end of the port connector having the diptube connector received therein is then slid into the free end of a delivery tube. In this configuration, fluid transfers from within the media bag into the diptube at the second thereof.

The fluid then travels through both the diptube, the channel of the diptube connector, and finally into the delivery tube from which it is subsequently dispensed.

By using the inventive design, only single barbed connectors are required. As a result, each of the connectors can be manufactured using injection molding processes without having a mold seam line that longitudinally extends across the barb of each of the connectors. As a result, the likelihood of contaminants passing between each of the barbs and their overlying tubes is decreased. Furthermore, the diptube connector is a relatively small component which can be easily manufactured having different sizes and which can be removed when a diptube is not required.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 2:
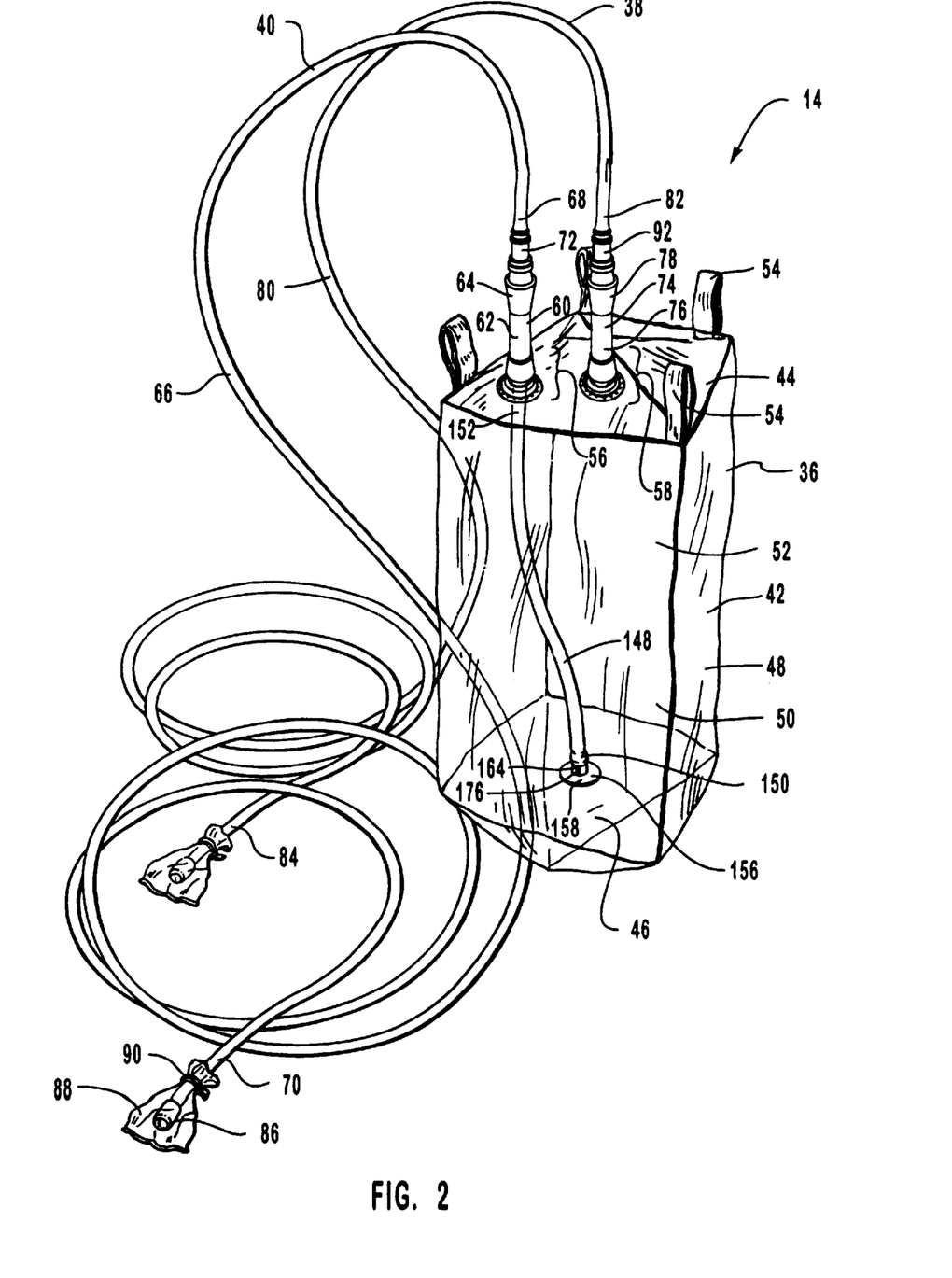
FIG. 2 is a perspective view of an inventive fluid delivery system.

Depicted in FIG. 2 is one embodiment of a fluid delivery system 14 incorporating features of the present invention. Fluid delivery system 14 generally comprises a collapsible media bag 36, a supply tube 38, and a delivery tube 40. Media bag 36 comprises a body wall 42 having a top end 44, a bottom end 46, an exterior surface 48, and an interior surface 50. Interior surface 50 defines a compartment 52 enclosed within media bag 36. Attached to media bag 36 at top end 44 are four loop handles 54. Also formed at top end 44 is a first port assembly 56 and a second port assembly 58. As will be discussed later in greater detail, port assemblies 56 and 58 are respectively used for attaching delivery tube 40 and supply tube 38 in fluid communication with compartment 52.

Body wall 42 of media bag 36 is preferably made of any thin, flexible plastic which can be used for storing chemicals, pharmaceutical fluids, biological fluids, or other fluids where the maintenance of a sterile environment is desired. Body wall 42 can comprise a single layer of material or, more preferably, a plurality of layers or liners. The multiple layers help to limit the potential of a leak which could contaminate the fluids positioned within media bag 36.

Delivery tube 40 has a lumen longitudinally extending therethrough and is depicted as comprising a transition tube 60 and a feeding tube 66. Transition tube 60 has a first end 62 attached to first port assembly 56 and an opposing second end 64. Feeding tube 66 has a first end 68 and an opposing free second end 70. Extending between first end 68 of feeding tube 66 and second end 64 of transition tube 60 is a first adapter 72 which will be discussed later in greater detail.

Similar to delivery tube 40, supply tube 38 also has a lumen extending therethrough and comprises a transition tube 74 and a source tube 80. Transition tube 74 further comprises a first end 76 attached to second port assembly 58 and a second end 78. Source tube 80 likewise has a first end 82 and an opposing free second end 84. A second adapter 92 is positioned between first end 82 of source tube 80 and second end 78 of transition tube 74.

Second end 84 of source tube 80 and second end 70 of feeding tube 66 are preferably manufactured so as to be hermetically sealed closed in a sterile condition. In one embodiment, a cap 86 is positioned over second end 70 while both cap 86 and a portion of second end 70 are received within a sterile bag 88. Bag 88 is sealed closed around feeding tube 66 by a plastic tie 90. Second end 84 of source tube 80 is sealed closed using substantially similar structure.

Since second end 84 of source tube 80 and second end 70 of feeding tube 66 are sealed closed, the lumens of supply tube 38 and delivery tube 40 in conjunction with compartment 52 of media bag 36 substantially define a closed sterile environment. As such, fluids can be delivered and removed from the closed sterile environment of fluid delivery system 14 without compromising the sterile nature of the fluid.

Fluid delivery system 14 can be used in a variety of different fashions for dispensing sterile fluid housed within media bag 36. for example, in one embodiment, media bag 36 can be supported within a rigid container, such as an barrel, by securing loop handles 54 to the inside of the barrel. A pump can then be attached to delivery tube for withdrawing fluid from media bag 36. Supply tube 38 can be used for filling media bag 36 with the sterile fluid. In alternative embodiment, media bag 36 can be made without supply tube 38. Alternative embodiments and further disclosure with regard to fluid delivery system 14 are disclosed in U.S. patent application Ser. No. 08/744,418 filed Nov. 8, 1996, now U.S. Pat. No. 5,799,830 entitled Pressure Vessel Access Port (hereinafter the '418 application) and U.S. patent application Ser. No. 08/331,696 filed Oct. 31, 1995, now U.S. Pat. No. 5,687,993 entitled Dual Containment Systems for Transferring Sterile Fluids to and From a Container which applications are incorporated herein by specific reference.

To extract fluid from within media bag 36, a diptube 148 has a first end 152 attached to port assembly 56 and a second end 150 mounted to bottom end 46 of media bag 36. Second end 150 of diptube 148 is attached to bottom end 46 of media bag 36 by an anchor 156. Anchor 156 comprises a mounting plate 158 having a tubular spout 164 upstanding therefrom. A plurality of side ports 176 extend through spout 164 so as to communicate with a passageway therein.

During use, anchor 156 is initially secured to media bag 36 by using conventional chemical or thermal processes to adhere mounting plate 158 to bottom end 46 of media bag 36. Spout 164 is then received within second end 150 of diptube 148 so that side ports 176 are openly exposed. In this configuration, diptube 148 is secured to the bottom of media bag 36 to enable fluid thereat to flow through side ports 176 and into diptube 148. Anchor 156 is further described in the '418 application previously incorporated by reference. In alternative embodiments second end 150 of diptube 148 can be freely suspended within media bag 56 such that anchor 156 is not required.

Figure 3:
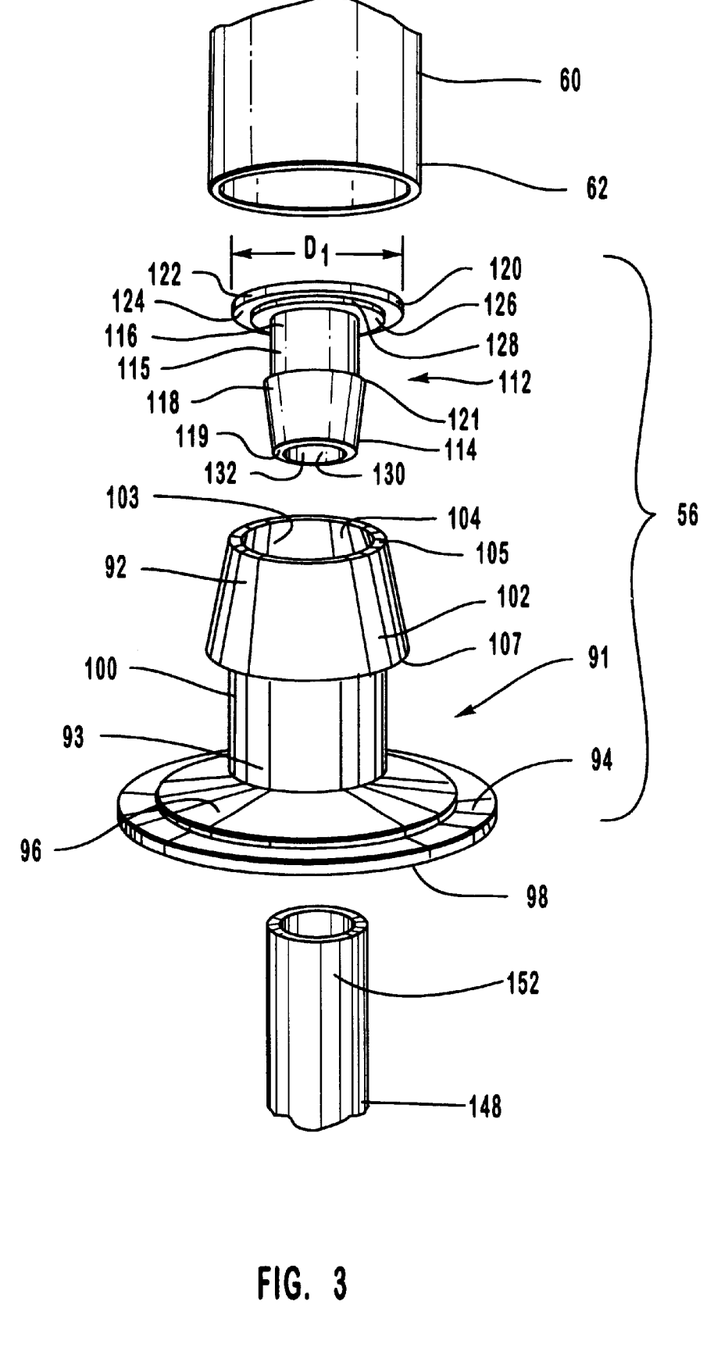
FIG. 3 is a perspective view of a disassembled port assembly used in the fluid delivery system shown in FIG. 2.

Depicted in FIG. 3, first port assembly 56 comprising a port connector 91 and a diptube connector 112. Port connector 91 has an outlet spout 100 extending from a first end 92 to an opposing second end 93. An interior surface 103 bounds a passageway 104 extending between ends 92 and 93. Radially projecting out from first end 92 is an annular barb 102. Barb 102 slopes outward from an end face 105 to an outside shoulder 107. Radially projecting out from second end 93 is a circular port plate 94. Port plate 94 has a top surface 96 and an opposing bottom surface 98.

Figure 4:
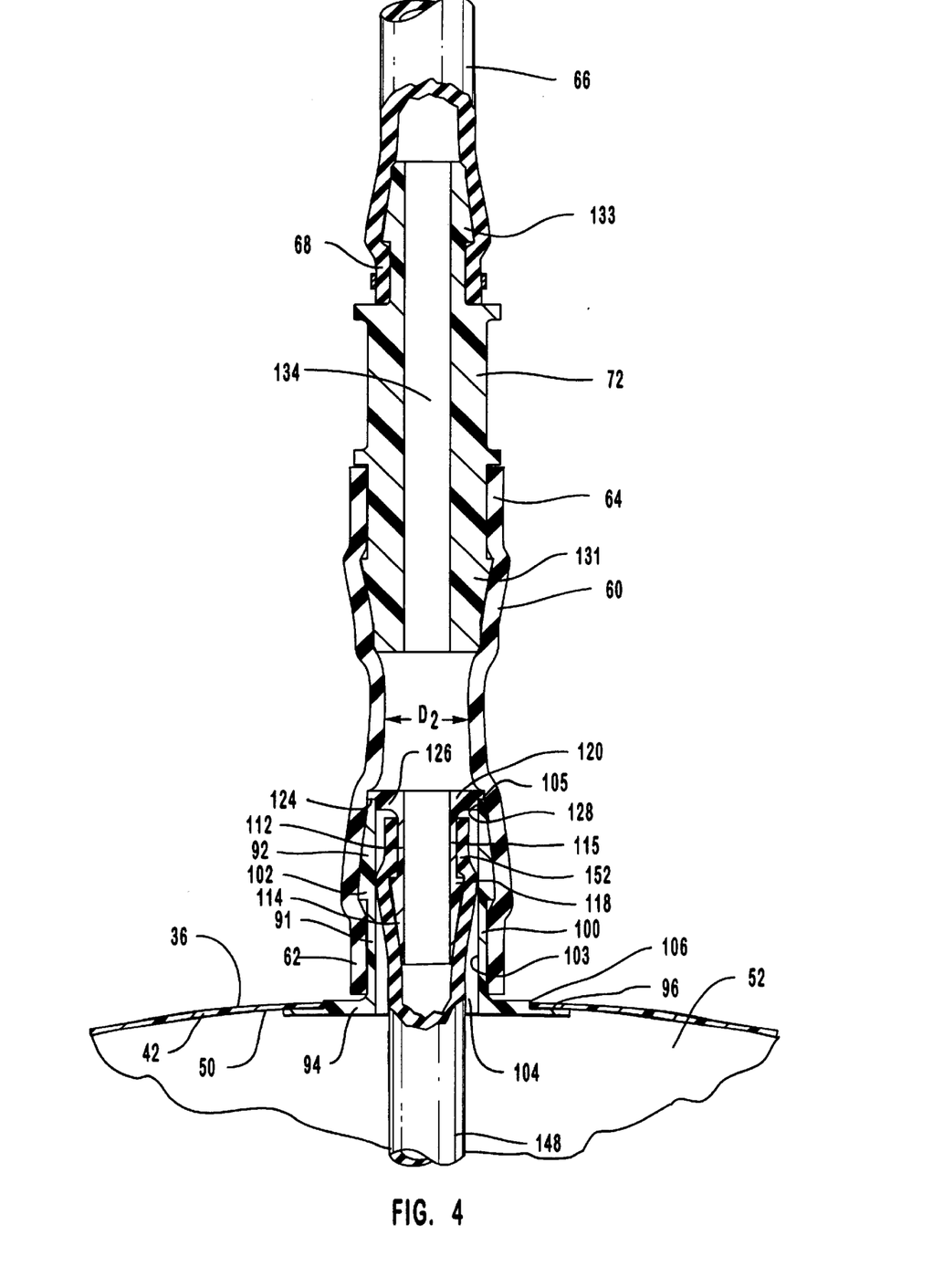
FIG. 4 is a cross-sectional side view of the port assembly shown in FIG. 3 in an assembled condition.

As depicted in FIG. 4, media bag 36 is initially formed with an aperture 106 extending therethrough. Prior to sealing compartment 52 closed, spout 100 is advanced from within compartment 52 through aperture 106. Top surface 96 of port plate 94 is then secured by conventional chemical or thermal methods against interior surface 50 of media bag 36.

The present invention also provides means removably mounted to spout 100 of port connector 91 for securing first end 152 of diptube 148 within passageway 104 of spout 100 so as to enable fluid to pass through diptube 148 and out spout 100. By way of example and not by limitation, depicted in FIG. 3, diptube connector 112 comprises a tubular stem 115 having a first end 114 and an opposing second end 116. An interior surface 130 bounds a channel 132 extending between ends 114 and 116. Radially projecting out from first end 114 is an annular barb 118. Barb 118 slopes outward from an end face 119 to an outside shoulder 121. Radially projecting out from second end 116 is a mounting flange 120. Mounting flange 120 comprises a circular primary plate 122 having an inside face 124. Primary plate 122 has an outer diameter Di that is larger than the inner diameter of passageway 104 in port connector 91. Projecting from face 124 is a circular secondary plate 126 having an outside shoulder 128. Secondary plate 126 is coaxially aligned with primary plate 122 and has an outer diameter smaller than the outer diameter of primary plate 122.

During assembly, as depicted in FIG. 4, port connector 91 is first attached to media bag 36 as previously discussed. Next, first end 114 of diptube connector 112 is slid within first end 152 of diptube 148. The lumen within diptube 148 is slightly smaller than barb 118 so that a sealed friction engagement is produced therebetween. If desired, a tie can be used to secure diptube 148 on stem 115. Once attached, second end 150 of diptube 148 is advanced through passageway 104 in port connector 91, into compartment 52, and attached, if desired, to anchor 156.

Stem 15 of diptube connector 112 is also received within passageway 104 of connector 91 such that end face 105 of port connector 91 is biased against face 124 of flange 120. In this position, secondary plate 126 is received within passageway 104 such that shoulder 128 is biased against interior surface 103 of port connector 91. In one embodiment, shoulder 128 is so sized as to produce a friction fit against port connector 91, thereby retaining diptube connector 112 against port connector 91 and also functioning as a seal that prevents liquid from passing therebetween.

Once diptube connector 112 is mounted to port connector 91, first end 92 of port connector 91 is received within first end 62 of transition tube 60. Barb 102 biases against the interior surface of transition tube 60 effecting a sealed engagement therewith. A tie can also be used to secure transition tube 60 to port connector 91.

In one embodiment of the present invention, means are also provided for biasing diptube connector 112 on first end 92 of outlet spout 100. By way of example and not by limitation, transition tube 60 is depicted as having an inner diameter $D_2$ that is smaller than outer diameter $D_1$ of mounting flange 120. Accordingly, once port connector 91 has been received within transition tube 60, transition tube 60 radially inwardly constricts to bias against mounting flange 120.

Adapter 72 has a singe first barbed end 131 and an opposing second barbed end 133. A passageway 134 longitudinally extends therebetween. First barbed end 131 is disposed in sealed, biased engagement within second end 64 of transition tube 60. Likewise, second barbed end 133 is disposed in sealed, biased engagement within first end 68 of feeding tube 66. Adapter 72 is not a necessary element to the system. In alternative embodiments, first end 68 of feeding tube 66 can be directly coupled to port connector 91. In one embodiment, however, barbed ends 131 and 133 of adapter 72 are different sizes, thereby enable a transition to different sized tubes to accommodate different flow rates.

Figure 5:
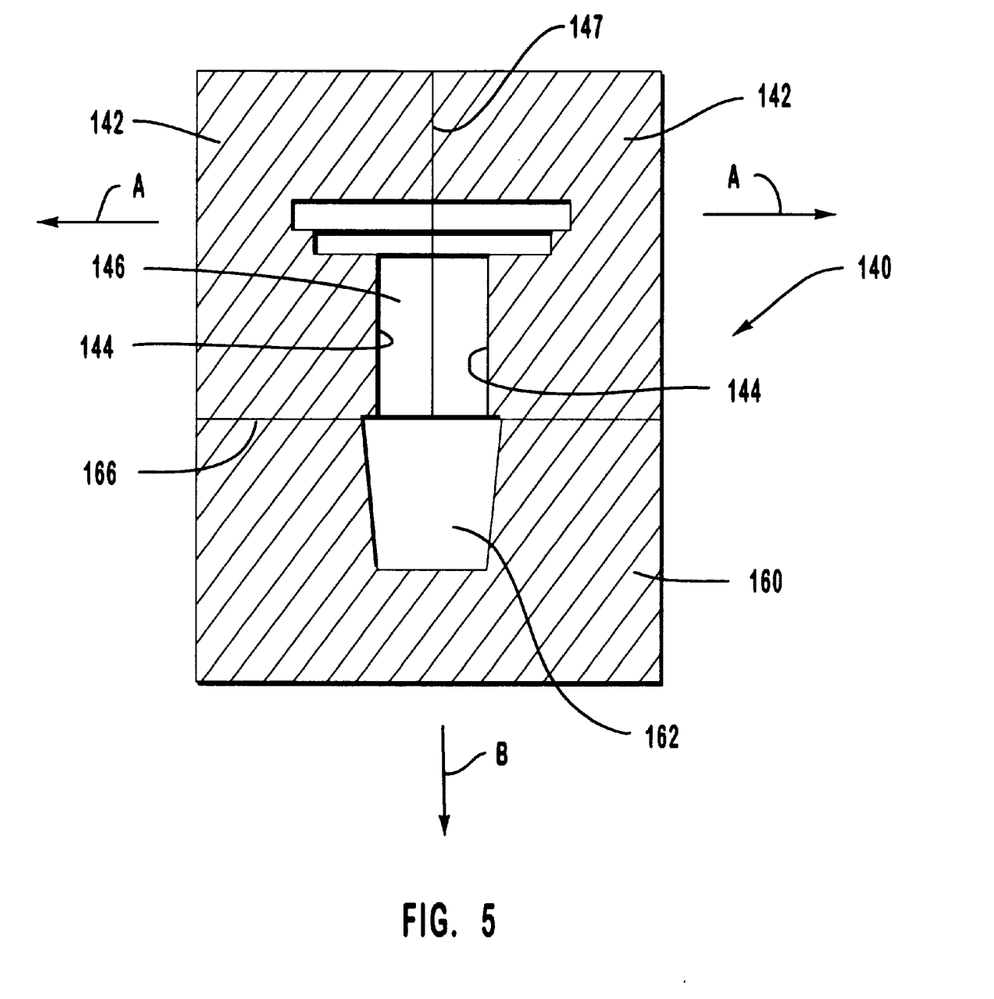
FIG. 5 is a cross-sectional side view of a multi-part mold used in making the diptube connector shown in FIG. 3.

As a result of connectors 91 and 112 each having only a single barb and adapter 72 only having a single barb at each end, these elements can be injection molded from plastic without having a seam line that longitudinally extends across the barbs. For example, as depicted in FIG. 5, diptube connector 1 12 can be made from a three piece mold 140. Mold 140 includes a pair of complementary upper dies 142 and a single lower die 160. Each of upper dies 142 has an interior surface 144 configured such that when dies 142 are coupled, a cavity 146 is formed having a configuration complementary to the shape of a portion of diptube connector 112 extending from barb shoulder 121 to mounting flange 120. With reference to FIG. 4, dies 142 mate together along longitudinally disposed joints 147 and can be separate horizontally along arrows A. As a result, mold seam lines longitudinally extend on resulting diptube connector 112 from barb shoulder 121 to mounting flange 120 along joints 147.

In contrast, lower die 160 has an internal cavity 162 with a configuration complementary to that portion of diptube connector 112 extending from barb shoulder 121 to end face 119. Lower die 160 couples with upper dies 142 along a horizontal joint 166 and can be downwardly separated from upper dies 142 along arrow B. During injection molding, a horizontal mold seam line is formed around barb shoulder 121 adjacent to joint 166. The benefit of this mold configuration, is that the mold dies can be separated without barb 118 being caught therein and also eliminates any seam lines being formed longitudinally across barb 118.

The mold assembly depicted in FIG. 5 is used to illustrate how the molds can be configured so that seam lines do not longitudinally extend across related barbs. Of course, the actual mold assembly will need to include a plug to form the channel 132 extending through diptube connector 112.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A port assembly for use with an interior compartment of a container, the port assembly comprising:
   (a) a diptube having a first end, an opposing second end, and a fluid path extending therebetween, the fluid path being open such that fluid can freely flow from the second end to the first end;
   (b) a tubular outlet spout having a free first end, an opposing second end, and an interior surface bounding a passageway extending therebetween, the second end of the outlet spout being adapted to be attached to the container such that the passageway communicates with the interior compartment of the container; and
   (c) a diptube connector comprising a tubular stem having a first end, an opposing second end, and an interior surface bounding a channel extending therebetween, the first end of the diptube connector being selectively received within the first end of the diptube, the first end of the diptube being received within the passageway of the outlet spout, the second end of the stem having a flange radially outwardly extending therefrom, the flange having an outer diameter greater than the inner diameter of the passageway at the first end of the outlet spout.

2. A port assembly as recited in claim 1, further comprising an annular barb radially outwardly projecting from the first end of the stem.

3. A port assembly as recited in claim 1, wherein the flange at the second end of the stem is annular.

4. A port assembly as recited in claim 3, wherein the flange comprises:
   (a) a primary plate having an outer diameter larger than the inner diameter of the passageway in the outlet spout; and
   (b) a secondary plate mounted against the primary plate and having an outside shoulder complementary to the interior surface of the passageway in the outlet spout.

5. A port assembly as recited in claim 1, further comprising an annular barb radially outwardly projecting from the first end of the outlet spout.

6. A port assembly as recited in claim 1, further comprising means for biasing the diptube connector on the first end of the outlet spout.

7. A port assembly as recited in claim 6, wherein the means for biasing comprises a flexible delivery tube having an end received over the first end of the outlet spout, the delivery tube having an inner diameter smaller than the outer diameter of the flange on the diptube connector.

8. A port assembly as recited in claim 1, further comprising a port plate radially extending out from the second end of the outlet spout.

9. A fluid delivery system comprising:
   (a) a container having an interior compartment;
   (b) a tubular outlet spout having a free first end, an opposing second end, and a passageway extending therebetween, the second end of the outlet spout being attached to the container such that the passageway communicates with the interior compartment of the container;
   (c) a diptube having a first end, a second end, and a fluid path extending therebetween, the first end terminating at a terminus disposed within the passageway of the outlet spout, the second end being in fluid communication with the compartment of the container, the fluid path of the diptube being open such that when fluid is disposed within the compartment of the container, the fluid can travel through the fluid path from the second end of the diptube to the first end of the diptube; and
   (d) means removably mounted to the outlet spout for securing the first end of the diptube within the passageway of the outlet spout so as to enable fluid to pass through the diptube and out the outlet spout.

10. A fluid delivery system as recited in claim 9, wherein the container comprises a flexible media bag.

11. A fluid delivery system as recited in claim 9, further comprising an annular barb radially outwardly projecting from the first end of the outlet spout.

12. A fluid delivery system as recited in claim 9, wherein the means for securing comprises a stem having a channel extending between a first end and an opposing second end, the first end of the stem being configured to be received within the first end of the diptube, the second end of the stem having a flange outwardly projecting therefrom, the flange having an outer diameter larger than the inner diameter of the passageway in the outlet spout.

13. A fluid delivery system as recited in claim 12, wherein the flange is annular.

14. A fluid delivery system as recited in claim 12, wherein the flange comprises:
   (a) a primary plate having an outer diameter larger than the inner diameter of the passageway; and
   (b) a secondary plate mounted against the primary plate and having an outer diameter complementary to the inner diameter of the passageway in the outlet spout.

15. A fluid delivery system as recited in claim 9, further comprising an annular port plate radially outwardly projecting from the second end of the outlet spout.

16. A fluid delivery system as recited in claim 9, further comprising a flexible delivery tube having an end received over the first end of the outlet spout, the delivery tube having an inner diameter smaller than the outer diameter of the flange on the diptube connector.

17. A fluid delivery system comprising:
   (a) a collapsible bag having an interior compartment;
   (b) a tubular outlet spout having a free first end, an opposing second end, and an interior surface bounding a passageway extending therebetween, the second end of the outlet spout being attached to the bag such that the passageway communicates with the interior compartment thereof:
   (c) a diptube having a first end, an opposing second end, and a fluid path extending therebetween, the first end being disposed within the passageway of the outlet spout, the second end being in fluid communication with the compartment of the collapsible bag, the fluid path of the diptube being open such that when fluid is disposed within the compartment of the collapsible bag, the fluid can travel through the fluid path from the second end of the diptube to the first end of the diptube; and
   (d) a diptube connector comprising a tubular stem having a first end, an opposing second end, and a channel extending therebetween, the first end of the diptube connector being removably received within the first end of the diptube when the first end of the diptube is received within the passageway of the outlet spout, the second end of the stem having a flange radially outwardly extending therefrom, the flange having an outer diameter greater than the inner diameter of the passageway at the first end of the outlet spout.

18. A fluid delivery system as recited in claim 17, further comprising an annular barb radially outwardly projecting from the first end of the stem.

19. A fluid delivery system as recited in claim 17, wherein the flange at the second end of the stem is annular.

20. A fluid delivery system as recited in claim 17, wherein the flange comprises:
(a) a primary plate having an outer diameter larger than the inner diameter of the passageway in the outlet spout; and
(b) a secondary plate mounted against the primary plate and having an outside shoulder complementary to the interior surface of the passageway in the outlet spout.

21. A fluid delivery system as recited in claim 17, further comprising an annular barb radially outwardly projecting from the first end of the outlet spout.

22. A method for assembling a fluid delivery system, the method comprising the steps of:
(a) securing a spout to a flexible media bag having an internal compartment, the spout having a passageway extending from a free end to the internal compartment of the media bag;
(b) inserting a tubular stem of a diptube connector into one end of a diptube, the diptube connector further comprising a flange outwardly projecting from an end of the stem outside of the diptube;
(c) disposing the diptube through the passageway in the spout so that the flange on the diptube connector rests on the free end of the spout, thereby supporting the diptube within the media bag; and
(d) positioning a delivery tube over the free end of the spout.

23. A method as recited in claim 22, wherein the step of positioning a delivery tube over the free end of the spout includes the delivery tube having an inner diameter smaller than the outer diameter of the flange on the diptube connector.

24. A port assembly for supporting a diptube within an interior compartment of a container, the port assembly comprising:
(a) a tubular outlet spout having a first end, an opposing second end, and an interior surface bounding a passageway extending therebetween, the second end of the outlet spout being adapted to be attached to the container such that the passageway communicates with the interior compartment of the container;
(b) a diptube connector comprising a tubular stem having a first end, an opposing second end, and an interior surface bounding a channel extending therebetween, the first end of the diptube connector being configured to selectively fluid couple with an end of the diptube when the first end of the diptube connector is received within the passageway of the outlet spout, the diptube connector also including a flange outwardly extending from the tubular stem, the flange being supported on the outlet spout when the first end of the diptube connector is received within the passageway of the outlet spout; and
(c) a delivery tube having a first end received over the first end of the outlet spout.

25. A port assembly as recited in claim 24, wherein the flange is disposed at the second end of the stem.

26. A fluid delivery system comprising:
(a) a container having an interior compartment;
(b) a tubular outlet spout having a first end, an opposing second end, and an interior surface bounding a passageway extending therebetween, the second end of the outlet spout being attached to the container such that the passageway communicates with the interior compartment thereof;
(c) a diptube having a first end and an opposing second end, the second end of the diptube being positioned within the interior compartment of the container;
(d) a tubular diptube connector having a first end, an opposing second end, and a channel extending therebetween, at least a portion of the diptube connector being disposed within the passageway of the tubular outlet spout, the first end of the diptube connector being fluid coupled with the first end of the diptube, the diptube connector being supported by the tubular outlet spout; and
(e) a transition tube having a first end received over with the first end of the outlet spout.

* * * * *

UNITED STATES PATENT AND TRADEMARK OFFICE
CERTIFICATE OF CORRECTION

PATENT NO. : 6,086,574
DATED : Jul. 11, 2000
INVENTOR(S) : David C. Carroll, Pat Draper It is certified that error appears in the above-identified patent and that said Letters Patent are hereby corrected as shown below:

Col. 4, line 37, after "36." change "for example" to --For example--

Col. 4, line 38, after "such as" change "an" to --a--

Col. 5, line 55, after "Stem" change "15" to --115--

Col. 6, line 31, after "connector" change "1 12" to --112--

Col. 10, line 39, after "over" delete "with"

Signed and Sealed this

Twenty-second Day of May, 2001

*Attest:*

NICHOLAS P. GODICI

*Attesting Officer*     *Acting Director of the United States Patent and Trademark Office*